(12) United States Patent
Shah et al.

(10) Patent No.: US 6,805,662 B2
(45) Date of Patent: Oct. 19, 2004

(54) URINARY INCONTINENCE CONTROL DEVICE AND METHOD OF USE

(75) Inventors: Tilak M. Shah, Cary, NC (US); Dezso K. Levius, Cary, NC (US)

(73) Assignee: Polyzen, Inc., Apex, NC (US)

( * ) Notice: Subject to any disclaimer, the term of this patent is extended or adjusted under 35 U.S.C. 154(b) by 0 days.

(21) Appl. No.: 10/368,184

(22) Filed: Feb. 18, 2003

(65) Prior Publication Data

US 2004/0162460 A1 Aug. 19, 2004

(51) Int. Cl.⁷ .................................................. A61F 2/00
(52) U.S. Cl. ......................................... 600/29; 128/885
(58) Field of Search ...................... 600/38–41, 29–32; 128/897, 898, 885; 606/201–202

(56) References Cited

U.S. PATENT DOCUMENTS

| | | | |
|---|---|---|---|
| 2,943,859 A | * 7/1960 | Koski | 473/214 |
| 4,066,084 A | * 1/1978 | Tillander | 606/202 |
| 4,399,809 A | * 8/1983 | Baro et al. | 600/31 |
| 4,626,250 A | 12/1986 | Schneider | |
| 4,710,169 A | * 12/1987 | Christopher | 604/104 |
| 4,800,900 A | 1/1989 | French | |
| 4,880,016 A | 11/1989 | Worth et al. | |
| 4,942,886 A | 7/1990 | Timmons | |
| 4,982,731 A | 1/1991 | Lue et al. | |
| 4,994,051 A | 2/1991 | Walsh | |
| 5,184,629 A | 2/1993 | Erickson et al. | |
| 5,211,640 A | 5/1993 | Wendler | |
| 5,295,946 A | 3/1994 | Collins | |
| 5,370,601 A | 12/1994 | Collins | |
| 5,415,179 A | 5/1995 | Mendoza | |
| 5,478,305 A | * 12/1995 | Craggs | 600/31 |
| 5,554,141 A | 9/1996 | Wendler | |
| 5,807,278 A | 9/1998 | McRae | |
| 5,823,972 A | 10/1998 | McRae | |
| 5,836,865 A | * 11/1998 | Ritchie et al. | 600/38 |
| 5,842,968 A | 12/1998 | Johnson | |
| 5,885,205 A | 3/1999 | Kassman | |
| 5,984,910 A | 11/1999 | Berke | |
| 6,015,379 A | 1/2000 | Sachse | |
| 6,113,532 A | * 9/2000 | Yap | 600/38 |
| 6,131,576 A | 10/2000 | Davis | |
| 6,138,678 A | 10/2000 | Nilsson | |
| 6,251,067 B1 | 6/2001 | Strickholm | |
| 6,289,895 B1 | 9/2001 | Cheng et al. | |
| 6,349,727 B1 | 2/2002 | Stewart, Jr. | |
| 6,460,541 B1 | * 10/2002 | Shah et al. | 128/845 |
| 6,463,932 B1 | 10/2002 | Single et al. | |
| 6,494,852 B1 | * 12/2002 | Barak et al. | 601/151 |
| 6,506,169 B2 | 1/2003 | Griffiths | |
| 2001/0005782 A1 | 6/2001 | Tanghoj et al. | |
| 2002/0087130 A1 | 7/2002 | Guldfeldt et al. | |
| 2002/0153014 A1 | 10/2002 | Cheng et al. | |

* cited by examiner

Primary Examiner—Samuel G. Gilbert
(74) Attorney, Agent, or Firm—Tristan A. Fuierer; Steven J. Hultquist; Marianne Fuierer (57) ABSTRACT

A male urinary incontinence control device including a circumferentially continuous inflatable cuff having a plurality of inflatable passages therein, optionally reinforced by rigid members, that slips over the glans of the penis for positioning along the longitudinal axis of the penile shaft. Upon inflation, the cuff applies radially inwardly directed compressive force to the shaft of the penis with a concomitant restriction of the urethral passageway. The inflatable cuff in one embodiment includes an integrated hand pump for convenient inflation and deflation.

44 Claims, 7 Drawing Sheets

URINARY INCONTINENCE CONTROL DEVICE AND METHOD OF USE

BACKGROUND OF THE INVENTION

1. Field of the Invention

The present invention relates generally to a device and method for controlling urinary incontinence of a male subject and more particularly to an inflatable cuff for restricting the urethral passageway and associated method for incontinence control.

2. Description of the Related Art

Male urinary incontinence is a long-recognized medical condition that poses an embarrassment to men whose urethral valves or sphincters are no longer capable of controlling the flow of urine from the bladder. Urinary incontinence can arise from a variety of causes, including disease, surgery, neurological dysfunction, malformation of the urethral valve, physical deterioration incident to advancing age, as well as various other causes. Externally applied absorbent pads and internal catheters connected to collection bags are currently used as solutions to the problem of incontinence. Such solutions, however, ultimately entail the external collection of the urine that escapes the bladder. Collection devices heretofore used for urine collection are frequently uncomfortable, inconvenient, unsanitary, offensive, unreliable and even inadequate during use.

Commonly employed non-invasive devices for the control of male incontinence include straps, bands, clamps, cradles, or other members that encircle the shaft of the penis. Devices of this type are positioned about and tightened around the shaft of the penis until sufficient pressure has been applied to the urethra and the corpus spongiosum to substantially and preferably completely close the urethra. The device is loosened or removed to permit the flow of urine through the urethra when appropriate.

The non-invasive type devices known in the art for controlling male incontinence can be flexible or rigid and frequently include a projection intended to lie beneath and apply a sealing pressure to the urethra and corpus spongiosum. The projection can be rigid or resilient, or can even be an inflatable sac. See, for example, U.S. Pat. Nos. 4,800,900, 5,984,910, 6,463,932. Inflatable sacs are also disclosed in erectile maintenance devices. See, for example, U.S. Pat. Nos. 5,295,946, 5,370,601, and 6,015,379.

Incontinence control devices of the encirclement type are designed to permit sufficient tightening of the device around the shaft of the penis, to prevent or substantially reduce the leakage of urine through the urethra. Unfortunately, sufficient tightening of the encirclement type device almost invariably results in the application of an excessive and not infrequently painful amount of pressure to tissues other than the urethra and corpus spongiosum. In particular, virtually all devices of this type apply undue pressure to the superficial dorsal vein, the deep dorsal veins, and the dorsal arteries and nerves. Accordingly, to avoid injury, such devices must be removed numerous times per day in order to reduce the applied pressure and allow proper blood flow.

Further, these male incontinence control devices do not always provide sufficient pressure to keep the urethra in a closed position. In particular, the penis and the urethra are both very flexible, and as such, the urethra can change location within the penis itself. Because prior devices employ means for applying preferential pressure to particular points on the penile shaft, any movement or improper positioning of the device along the shaft can result in an improperly closed or pinched urethra and the undesired occurrence of urine leakage.

Compressive encirclement devices for male incontinence control are subject to other drawbacks as well. Some are relatively complex in construction, and therefore relatively expensive to manufacture. Some provide poor adjustability to the particular patient using them. Further, many of these devices are very large and cumbersome. The size and weight of these devices results in such discomfort that the user is not able to wear the device for extended periods of time.

In light of the above, there is a continuing need for an improved device for controlling male urinary incontinence, which avoids applying undue pressure to the veins, arteries, and nerves of the penis shaft, while ensuring that sufficient pressure is applied to the urethra and the corpus spongiosum to prevent or substantially reduce leakage from the urethra. The desired device would avoid inflicting pain, trauma and/or damage to the skin and underlying tissues of the penile shaft when used, and preferably could be comfortably worn by the patient for extended periods of time, e.g., an entire day without removal, except for urination. There is a need for a device of such type that is relatively inexpensive in construction, easy to clean, and relatively easy to properly position on the penile shaft and to release for urination.

SUMMARY OF THE INVENTION

The present invention relates to a device and method for controlling urinary incontinence of a male subject.

In one aspect, the present invention relates to a male urinary incontinence control device comprising an inflatable cuff including a sealable interior volume having a valve associated therewith.

In another aspect, the present invention relates to an inflatable cuff adapted to slip over the glans of a penis wherein the inflatable cuff encircles the shaft of the penis along the longitudinal axis of the shaft. The inflatable cuff comprises an inner layer and an outer layer connected to form a sealable interior volume and a valve for introducing a fluid, such as air, into the sealable interior volume. The sealable interior volume comprises a plurality of inflatable interconnected passages arranged parallel to one another along the longitudinal axis of the cuff. In one embodiment, at least one of the inflatable passages comprises a rigid member wherein the rigid member extends along the longitudinal axis of the cuff. The outer layer of the inflatable cuff is substantially non-distensive and the inner layer is distensive and provides a variable inner diameter. Upon introduction of fluid into the inflatable passages, the variable inner diameter of the inner layer is reduced, thereby causing an increase in the circumferential pressure on the shaft of the penis, concomitantly closing the urethra and corpus spongiosum and preventing leakage.

In yet another aspect, the present invention further comprises an occlusive sac that is integrated into the inflatable cuff structure, for applying preferential pressure ventrally to the urethra and corpus spongiosum of the penis.

The present invention in another aspect further comprises a hand pump for inflating the sealable interior volume of the inflatable cuff. In a particularly preferred embodiment, the hand pump circumscribes the outer layer of the inflatable cuff, forming a unitary cuff-pump structure, wherein the hand pump means are communicatively connected to the valve of the inflatable cuff.

In a further embodiment, the inflatable cuff further is constructed and arranged for coupling to an external catheter for transporting urine from the penis to a collection container. The external catheter is preferably matably and removably attached to a distal end of the cuff.

The invention also relates in another aspect to a method of controlling urinary incontinence utilizing a device of a type as variously described above.

Other aspects, features and embodiments of the invention will be more fully apparent from the ensuing disclosure and appended claims.

DETAILED DESCRIPTION OF THE INVENTION, AND PREFERRED EMBODIMENTS THEREOF

The inflatable penile cuff of the present invention comprises a multilayer arrangement of polymeric film that is sealed to define an enclosed sealable interior volume, and a valve wherein the outlet end of the valve is positioned within the interior volume of the inflatable penile cuff.

In one embodiment, the cuff is comprised of a non-distensive outer layer and a distensive inner layer that provides a variable inner diameter. Preferably, the outer layer and inner layer are heat sealed along the circumference of the cuff at a location other than the distal end or proximal end of the cuff to ensure that the penis is not exposed to rough edges that can result in chafing or rubbing. Preferably, the inner layer overlaps the outer layer and the layers are sealed along the circumference of the outer layer, most preferably about 2 mm to about 25 mm from the distal or proximal end.

The inner and outer layers can therefore be provided as panels, e.g., generally rectangular in shape, of a polymeric material such as polyurethane or reinforced polyurethane film, that are selectively bonded at their registered margins and bonding lines for forming passages or pockets, as hereinafter described more fully, to form an interior volume that is fluid-tight and compartmented with the inflatable passages or pockets, so as to exert a circumferentially continuous compressive action on the penis when the interior volume and passages therein are inflated. The passages are preferably interconnected in gas communication with one another so that all passages are able to be inflated at the same time when inflation gas is introduced into the interior volume of the cuff. In one embodiment, at least one of the passages is arranged with stiffening element(s) therein, to rigidify the cuff and enable circumferential and longitudinal compression on the penis to be more effectively applied.

The bonding of the inner and outer layers of the cuff body can be effected in any suitable manner, e.g., by thermal bonding, such as radio-frequency heat sealing, by solvent bonding, adhesive bonding, etc.

The enclosed interior volume comprises inflatable interconnected passages that extend longitudinally in a direction parallel to the longitudinal axis of the inflatable cuff. The multiplicity of inflatable interconnected passages permits the cuff to be inflated in a manner that effects and maintains compressive action on the penis of a wearer, in a highly uniform manner about the entire circumference of the penis, as compared to a cuff lacking such interconnected passages. While the invention is described herein in reference to a preferred array of passages that are longitudinally extended, it will be recognized that the multiplicity of interior volume passages of the cuff can be of any other suitable geometry or conformation, e.g., linear, curvate, or non-linear, serpentine, zig-zag, spiral, labyrinthine, etc.

In one preferred embodiment, at least one of the inflatable interconnected passages contains a rigid member, wherein the rigid member extends longitudinally in a direction parallel to the longitudinal axis of the cuff. In another particularly preferred embodiment, the inner layer, outer layer and valve are formed of the same polymeric film material, such as polyurethane or reinforced polyurethane.

The penile cuff advantageously is fabricated as a circumferentially continuous tubular body that slides over the glans of a flaccid penis for placement on the shaft, so that the cuff extends longitudinally along the shaft of the penis, e.g., along a major portion of the length of the penile shaft, with the length of the penile cuff generally being in a range of from about 3 to about 6 inches. Once positioned on the shaft of the flaccid penis, the cuff can be filled with a fluid, preferably air, thereby reducing the variable inner diameter of the inner layer and concomitantly increasing the circumferential pressure on the shaft of the penis. With the increase in circumferential pressure, the urethra and corpus spongiosum is closed off, with concomitant prevention of urinary leakage.

It will be appreciated that prior or subsequent to inflation, the penile sheath can be stored or transported in a (deflated) compact state.

For the purposes of the present invention, "distal end" refers to the end of the cuff that is nearest the glans when the cuff is installed on the penis of a wearer. The "proximal end" refers to the end of the cuff that is nearest the pubic bone when the cuff is installed on the penis of a wearer. The "longitudinal axis" refers to the axis of the cuff that is coincident with the longitudinal axis of the penis when the cuff is installed on the penis of a wearer. "Fluid" can be any liquid or gas.

The inflatable cuff and the valve can be formed of any suitable materials of construction, but preferably are formed of a polymeric film having a low modulus and a rubbery "hand" character. The modulus (here meaning the modulus of elasticity at 50% elongation), is suitably below about 1500 pounds per square inch (psi), preferably being in the range of from about 50 to about 800 psi, and most preferably in the range of from about 50 to about 500 psi.

The durometer value of the polymeric film for such inflatable cuff is suitably below 98 A, being advantageously in the range of from about 10 to about 90 A, more preferably in the range of from about 20 to about 85 A, and most preferably from about 30 A to about 75 A.

Among polymeric film materials useful in the broad practice of the present invention to form the inflatable cuff and the valve, illustrative materials include: polyurethane; styrene-isoprene-styrene/styrene-butadiene-styrene compositions, such as Kraton® polymers (commercially available from Shell Chemical Company, Houston, Tex.); polyvinylchloride (PVC) that has been plasticized to the desired flexibility and hand characteristics; urethane/PVC blends; urethane that has been plasticized to the desired flexibility and hand characteristics; Covale™ polymer (commercially available from Dow Chemical Company, Midland, Mich.); polyester elastomers such as Hytrel® (commercially available from E.I. DuPont de Nemours & Company, Wilmington, Del.); polyamide elastomers such as Pebax® (commercially available from Atochem); olefinic polymers (polypropylene, polyethylene, etc.); and metallocene polymers.

A preferred polymeric film material is polyurethane film having a durometer not exceeding about 90 A.

The polymeric film material used to fabricate the inflatable cuff may be used in the form of a blown film, extruded sheet, solvent cast film or other suitable web stock formed of the polymeric material. In addition to the aforementioned polymeric materials, the inflatable cuffs of the invention may be formed of any other suitable materials, natural or synthetic, that in native form or as treated by suitable treatment methods, possess a sufficiently low gas permeability to be useful for their intended purpose, as regards the maintenance of the inflated condition for the desired duration.

The thickness of the polymeric film material used to form the inflatable cuff of the invention, in a preferred aspect, is typically in a range of from about 1 to about 25 mils, more preferably in a range of from about 2 to about 10 mils, and most preferably in a range of from about 2 to about 6 mils.

The polymeric film from which the inflatable cuff is fabricated can contain dye or pigment additives to impart a desired color to the product structure, and the resins from which the films are formed may be blended with other additives, such as tackifiers, antioxidants, uv stabilizers, dispersing agents, fillers, surfactants, surface modifiers, heat stabilizers, flame retardants, antimicrobial agents, etc., as necessary or desirable to the end use of the inflatable cuff. The sheet stock used to fabricate the inflatable cuff can also contain conductive material, e.g., carbon black or metallic particulate materials, to impart conductivity characteristics to the cuff, if desired in a specific end use application of the invention.

The inflatable cuff of the invention can be readily formed by heat-sealing or seam joining techniques commonly known and used in the art for forming structural articles from polymeric film materials in the form of web or sheet stock. For example, the laminae of the inflatable cuff of the present invention can be joined by a suitable welding technique such as RF welding, heat impulse welding, solvent welding, adhesive bonding, etc. It is also possible to join the respective layers of the structure by adhesive bonding or any other suitable joining means and methods. Preferably, heat impulse welding or RF welding is employed, with RF welding being most preferred.

The sealable interior volume of the inflatable cuff may have any suitable volume appropriate to its use. In one embodiment, the interior volume can have an interior inflated volume in a range of from about 0.05 liter to about 2 liters. It will be recognized that the inflated volume of the cuff compartment will depend on the pressure to which the compartment is inflated, and the extensibility or expandable character of the compartment. In the case of elastomeric or elastic materials of construction, the volumetric expansion of the cuff inflation compartment may be significant.

The seams of the inflatable cuff themselves must be continuous along their length, to provide the requisite leak-tightness for the product article in the inflated condition. Preferred seam characteristics for polyurethane materials of the above-described types, include a seam dimension that is in a range of from about 0.020 to 0.250 inch, and most preferably in a range of from about 0.050 to about 0.125 inch.

In preferred practice, the seam strength of the inflatable cuff should be at least about 1000 pounds per square inch (psi), or alternatively at least about 30% of the strength of the unwelded film.

It will be appreciated that the longitudinal length of the cuff and the uninflated inner diameter of the cuff can be varied depending on the flaccid penis length and thickness.

The interconnected passages of the interior volume of the cuff can be formed by suitable sealing techniques, e.g., radio frequency sealing or other heat sealing technique, solvent or adhesive bonding, etc., to form pockets that can be selectively inflated when inflating fluid is introduced to the interior volume of the cuff, and from which inflation fluid can be withdrawn during deflation of the interior volume of the cuff. The interconnected passages can be interconnected in any way to one another, e.g., by one or more openings of the passages by means of which gas introduced to the interior volume of the cuff is able to flow into the passages.

In one conformation, the passages are elongate in character and generally parallel to the longitudinal axis of the cuff, being circumferentially spaced apart from one another by longitudinally extending seams bounding circumferentially adjacent passages. The seam width can be of any suitable dimension in relation to the width of the constituent interconnected passages of the cuff. In one embodiment, such seam width is in a range of from about 0.1 to about 1.5 times the width of the passages adjacent to such seam.

The rigid member(s) utilized for structural reinforcement of the cuff can comprise strips of plastic, textile material, rubber, wood, metal, etc., and can be glued on, sewn on, packed in pockets, or woven into the interior volume itself. The width of the rigid members can vary depending on the diameter and circumference of the inflatable cuff. Additionally, the spacing of the rigid members relative to one another can vary. For example, the rigid members can be circumferentially spaced apart from one another, by a spacing distance that can be approximately equal to the width of the rigid members.

The valve utilized in the cuff can be of any suitable type, but is preferably an anti-reflux valve, as more fully described in U.S. Pat. No. 6,460,541 issued to the present inventors, the disclosure of which is hereby incorporated herein by reference in its entirety for all purposes. Additional valve types that can alternatively be employed to advantage in the practice of the invention include check valves and other one-way valves. As discussed hereinabove, the valve can be formed of a same material as the inner layer and outer layer of the sealable interior volume, and the valve preferably has a size that enables a highly compacted character of the cuff article to be achieved, upon deflation of the cuff article for storage and transport. Since the cuff must be at least partially deflated when the user wishes to urinate, the valve is advantageously of a type that allows for convenient inflation and ready deflation.

The pump for inflating the cuff can be of any suitable type, including for example, and without limitation, hand pumps, such as pressure bulbs, bellows, and the like, as well as compressed gas supplies such as tanks or other vessels containing compressed air or other compressed gas as an inflation gas, optionally including inflation lines, flow control valves, etc.

In a preferred aspect, the penile cuff is fabricated so that it does not slip along the shaft of the penis once properly located and installed. This non-slip character can be achieved by applying a low-tack skin-bonding spray adhesive to the shaft prior to cuff positioning. Alternatively, the inner layer may be slip-resistant. For example, the inner layer of the inflatable cuff may be comprised of a non-slip waterproof fabric, such as expanded polytetrafluoroethylene (ePTFE), as described in Crawley, et al., U.S. Pat. No. 5,948,707. Alternatively, the inner layer film may be chemically or physically modified on its skin-contacting surface to impart slip-resistance characteristics, by surface treatment such as ionization treatment, chemical etching, abrasion techniques, texturizing techniques, surface application of tackifiers, etc.

Figure 1:
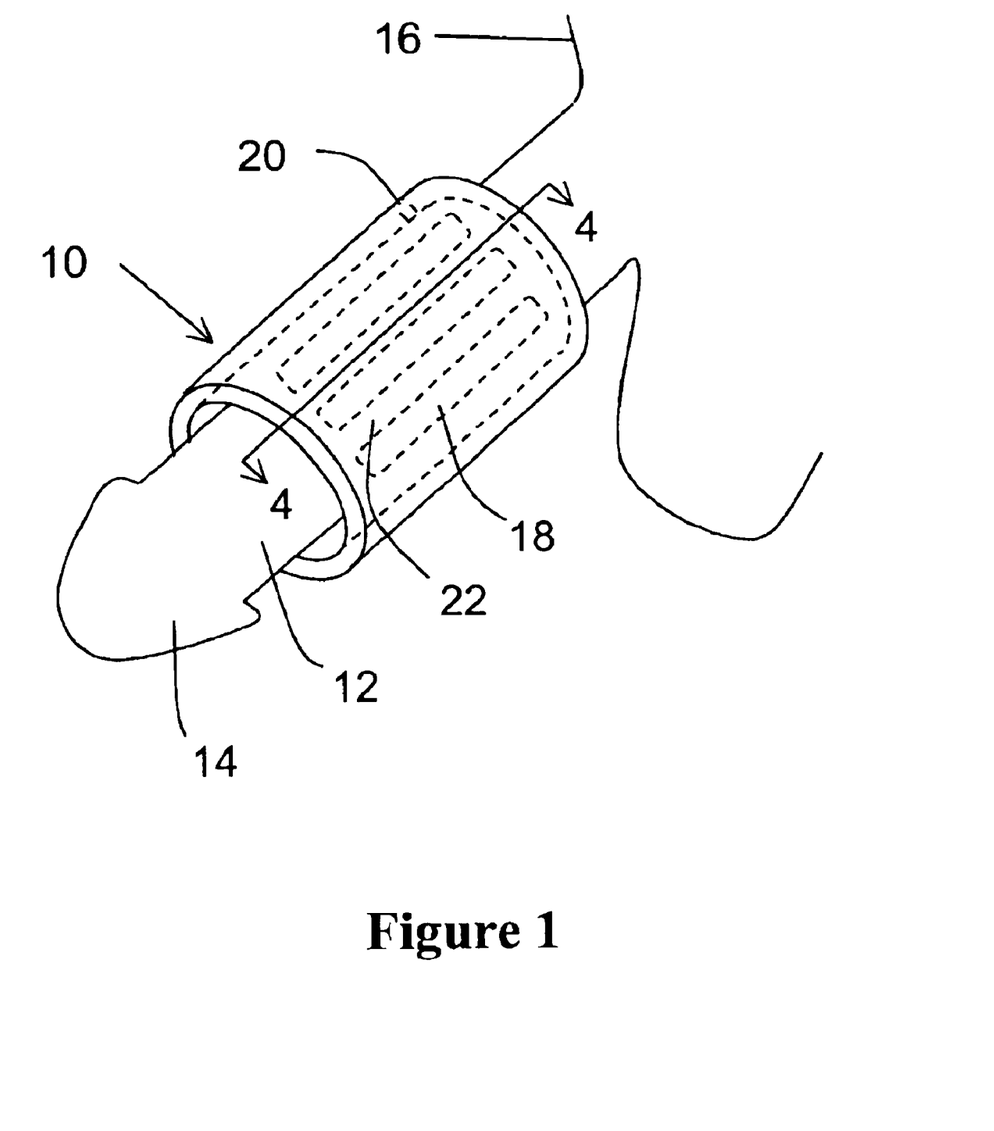
FIG. 1 is a perspective view of a male urinary incontinence device according to one embodiment of the present invention.

Referring now to the drawings, FIG. 1 is a perspective view of the uninflated penile cuff 10 according to one embodiment of the invention. The cuff as illustrated is slid over the glans 14 and positioned on the penile shaft 12 between the glans 14 and the pubic bone 16 of the wearer. The rigid members 18 are shown in phantom dashed line representation, extending in a direction that is parallel to the longitudinal axis of the wearer's penis and the longitudinal axis of the cuff 10. The inflation valve 20 is located at the proximal end portion of the cuff, but can alternatively be positioned along the length of the cuff, or as a still further alternative the inflation valve can be disposed at a distal end portion of the cuff, as desired in a given application of the invention.

For this purpose, the cuff 10 is formed with an inner and outer sheet bonded to one another to form a fluid-tight inflation cavity circumscribing the exterior surface of the penis, and constructed so that the inflation cavity of the cuff can be filled with inflation gas via valve 20.

The inflation valve 20 can be of any suitable type, and is desirably quickly and easily coupleable to an inflation gas source, such as a pump, compressor, pressurized gas storage and dispensing vessel, or the like, as coupleable with the valve inlet by suitable coupling structure, such as a gas flow line, nozzle, injection head, or the like. Upon inflation, fluid will enter the cuff 10 filling in the spaces 22 around the rigid members 18. Desirably, the open proximal and distal ends of the cuff have smooth bounding surfaces around each opening, to ensure comfort of the wearer when the cuff is inflated and in use. For this reason, it is preferred that the respective proximal and distal end openings are bounded by longitudinally overlapping of one of the layers forming the cavity over the other layer, so that smooth and unseamed surface of the layer is presented at the end edge peripherally bounding the respective end opening.

Figure 2:
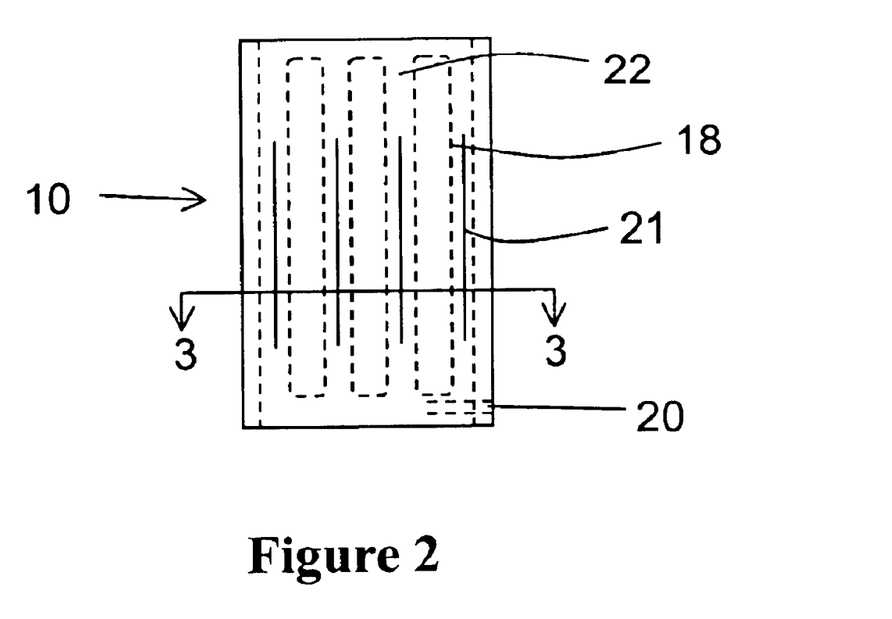
FIG. 2 is a top plan view of the uninflated male urinary incontinence device shown in FIG. 1.

FIG. 2 is a top plan view of the uninflated cuff 10 shown in FIG. 1. As shown in this view, rigid elongate members 18 are disposed between the two layers forming the cuff, in the inflatable cavity, being fixedly positioned against lateral movement by welds 21. The welds 21 define inflatable interconnected passages in the inflatable cavity. Upon inflation, fluid fills the spaces 22 around the welds 21 and the rigid elongate members 18.

Figure 3:
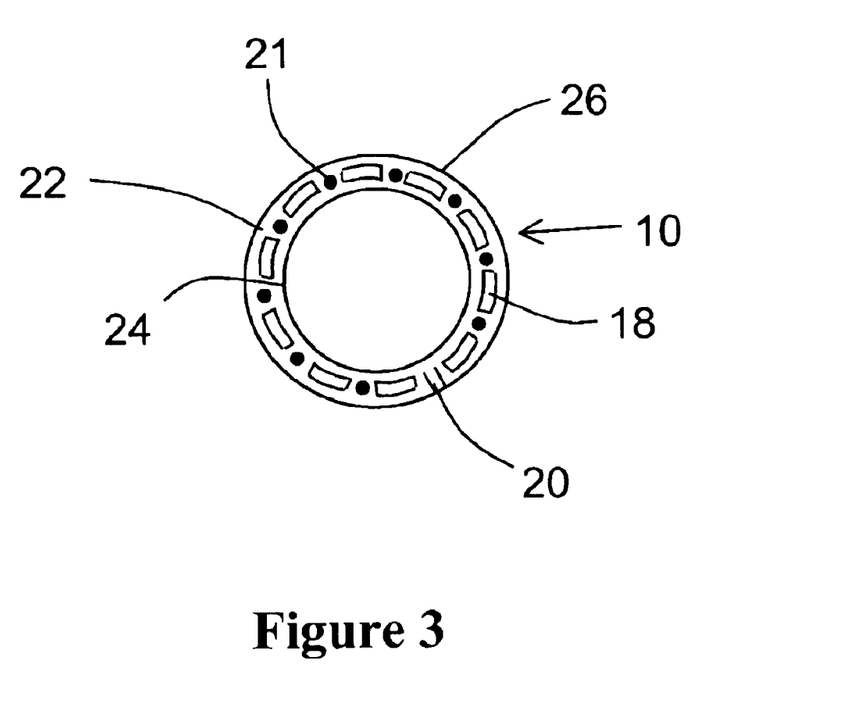
FIG. 3 is a cross sectional elevation view of the male urinary incontinence device shown in FIG. 2, taken along line 3—3 thereof.

FIG. 3 is a cross-sectional elevation view of the cuff 10 shown in FIG. 2, taken along line 3—3 thereof, showing the inner layer 24 and the outer layer 26 of the cuff, which define an interior volume therebetween containing the rigid elongate members 18 and the welds 21 demarcating the aforementioned inflatable passages.

Figure 4:
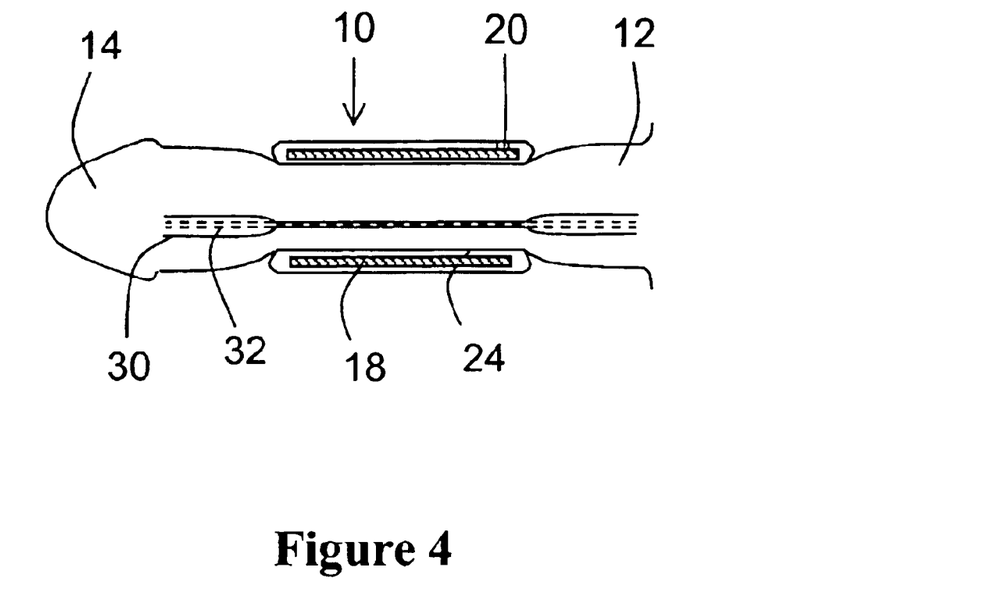
FIG. 4 is a cross sectional view of the inflated male urinary incontinence device shown in FIG. 1, taken along line 4—4 thereof.

FIG. 4 is a cross sectional view of the cuff shown in FIG. 1, taken along line 4—4 thereof, following inflation of the cuff with an inflation fluid. It can be seen that the portion of the penile shaft 12 circumscribed by the cuff 10 experiences circumferential pressure thereby closing off the urethra 32 and the corpus spongiosum 30. Because the rigid members 18 are symmetrically located about the circumference of the cuff, in circumferentially spaced-apart relationship to one another, specific placement of the cuff over the dorsal vein is not necessary. This is especially advantageous as it minimizes the risk of user error, in achieving effective leakage prevention.

The cuff as shown in FIG. 1 through FIG. 4 can be inflated using any external pump or compressed gas source, connecting tubing, etc.

Figure 5:
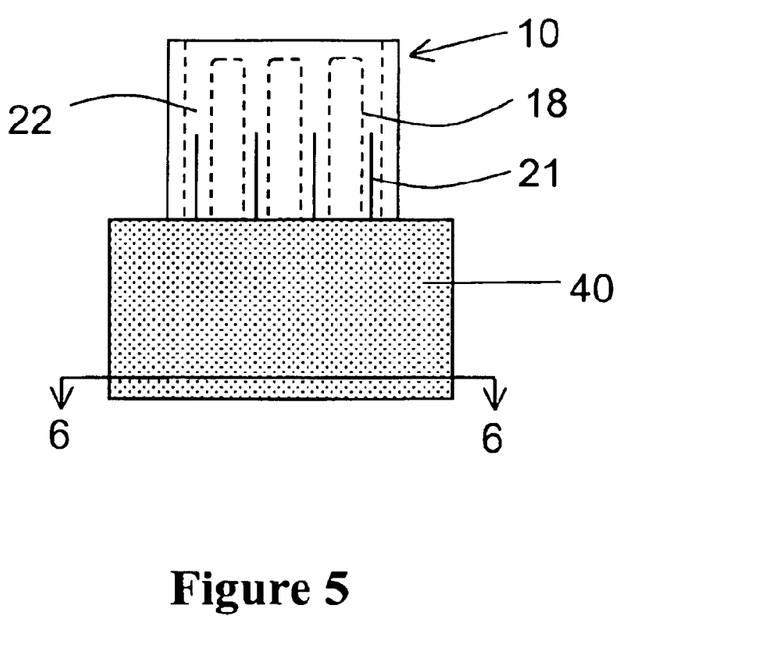
FIG. 5 is a top plan view of an alternative embodiment of the male urinary incontinence device of the present invention.

In one embodiment, shown in FIG. 5, a hand pump is integrated into the penile cuff. FIG. 5 is a top plan view of such alternative embodiment of the cuff 10 wherein a hand pump 40 is integrated into the inflatable cuff. The hand pump 40 can be located at any suitable location of the cuff, but preferably is located at either the distal end portion or the proximal end portion of the cuff.

Figure 6:
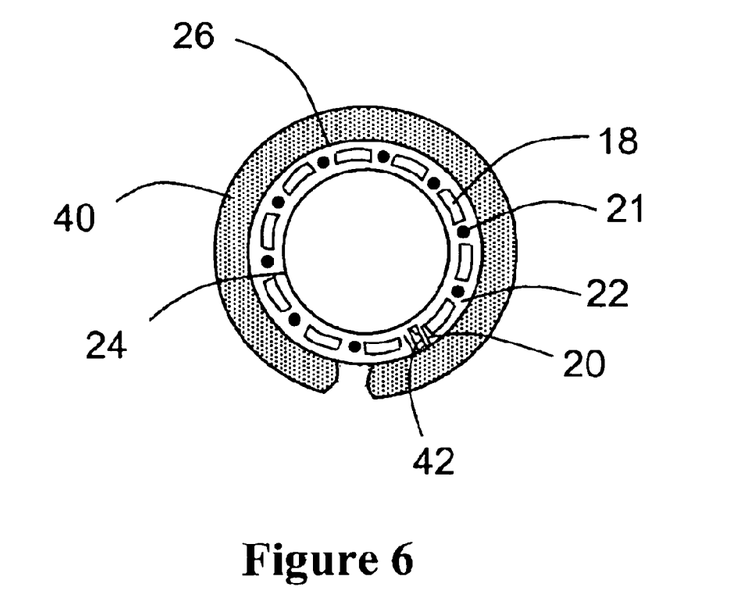
FIG. 6 is a cross-sectional elevation view of the male urinary incontinence device shown in FIG. 5, taken along line 6—6 thereof.

The integrated hand pump is further illustrated in FIG. 6, which is a cross-sectional elevational view of the cuff shown in FIG. 5, taken along line 6—6 thereof. It can be seen that the hand pump 40 circumscribes the cuff 10 along the outer cuff layer 26. The pump can completely encircle the entire circumferential extent of the outer layer 26 or alternatively it can encircle only an arcuate (<360°) portion of the outer layer of the cuff, as in the illustrative embodiment shown. In this embodiment, the pump valve 42 is communicatively connected to the inflatable cuff valve 20. This provides a built-in pump coupling whereby the wearer can rapidly inflate the cuff for use by repeatedly squeezing on the hand pump.

In one embodiment, the integrated hand pump 40 of FIG. 5 and FIG. 6 comprises an outer sheath that is perforate in character to allow ingress of ambient air upon squeezing. Disposed inside the sheath is an open cell foam material that traps air in its pores and expels the air into the cuff interior volume upon squeezing of the hand pump (the action of the hand in overlying the sheath surface during hand pumping serving to close the holes in the sheath to egress of air from the interior space of the sheath to the ambient environment). In this manner, the requisite volume of inflation air can be introduced into the interior volume of the cuff. By integrating the hand pump with the inflatable cuff, a unitary device is provided, that is easy to operate.

Additionally, by such integrated arrangement, the unitary device is continually at the ready for increasing the inflation (pump-up) if the cuff should partially deflate over an extended wearing period as a consequence of cumulative leakage through the seams or the sheet material of the cuff device.

Figure 7:
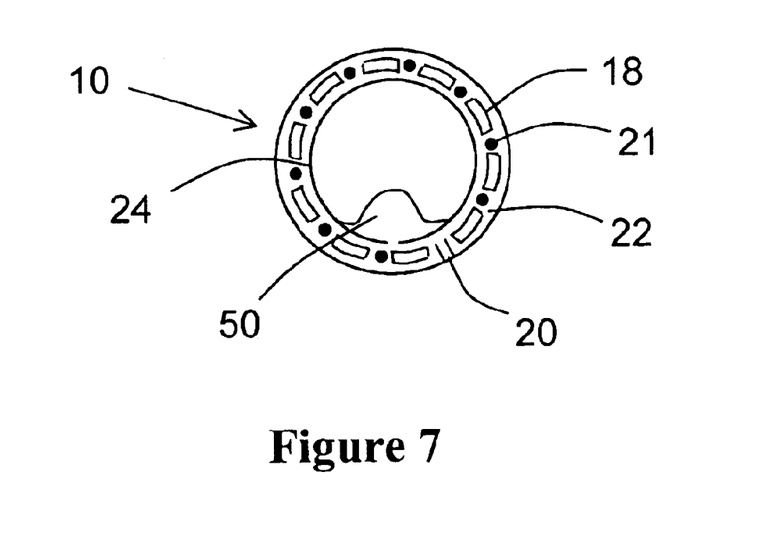
FIG. 7 is a cross-sectional elevation view of another embodiment of a male urinary incontinence device of the present invention.

FIG. 7 is a cross-sectional elevation view of another alternative embodiment of an inflatable cuff 10 according to the present invention. An occluder sac 50 is provided at the interior wall of the inner layer 24 of the cuff, for preferential placement ventrally, over the urethra and corpus spongiosum, prior to inflation. The occluder sac is formed by a third layer of material that can be bonded to the inner layer 24 at circumferentially spaced-apart regions of the inner layer surface, as shown, with such third layer of material extending along the length of the cuff at one region of the lumen opening defined by the cuff, so that a longitudinally extending occluder sac is provided inside the cuff. As inflation of the cuff occurs, air will enter the occluder sac and radially inwardly expand it, thereby providing additional pressure (relative to the circumferential pressure exerted by the inflated cuff between the first and second layers) on the urethra. The specifically located additional compressive force on the urethra from the occluder sac will ensure additional protection in preventing urine leakage in patients, e.g., those with advanced stages of urinary incontinence.

Figure 8:
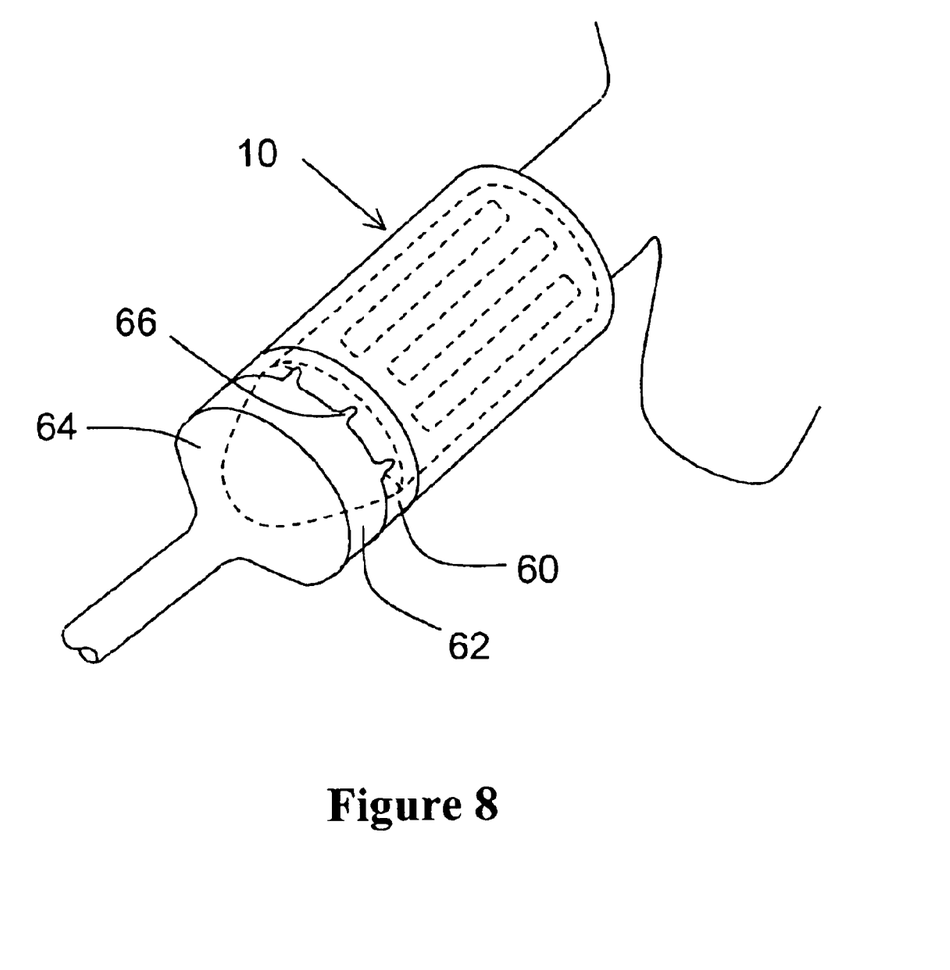
FIG. 8 is a perspective view of another embodiment of a male urinary incontinence device, comprising an inflatable cuff and an external catheter.

FIG. 8 is a perspective view of another embodiment of the penile sheath, comprising an inflatable cuff 10 matably attached by coupling elements 66 (schematically illustrated in simplified form in the drawing) to an external catheter 64.

In such embodiment, a first coupling 60 ring is bonded or otherwise secured to the distal end of the cuff 10, and such coupling ring is provided with coupling elements that are matably engageable with the coupling elements 66 of the catheter 64. The external catheter 64 has a second coupling ring 62, bearing the coupling elements 66.

The external catheter 64 comprises a narrow drainage tube leading to a collection bag, drain, or other urine collection or disposal structure or device. Because of the matable coupling feature, users can easily attach or remove the external catheter depending on their location and situation. The external catheter coupling structure is further illustrated in FIG. 9, which is a top plan view of the inflatable cuff shown in FIG. 8.

Figure 9:
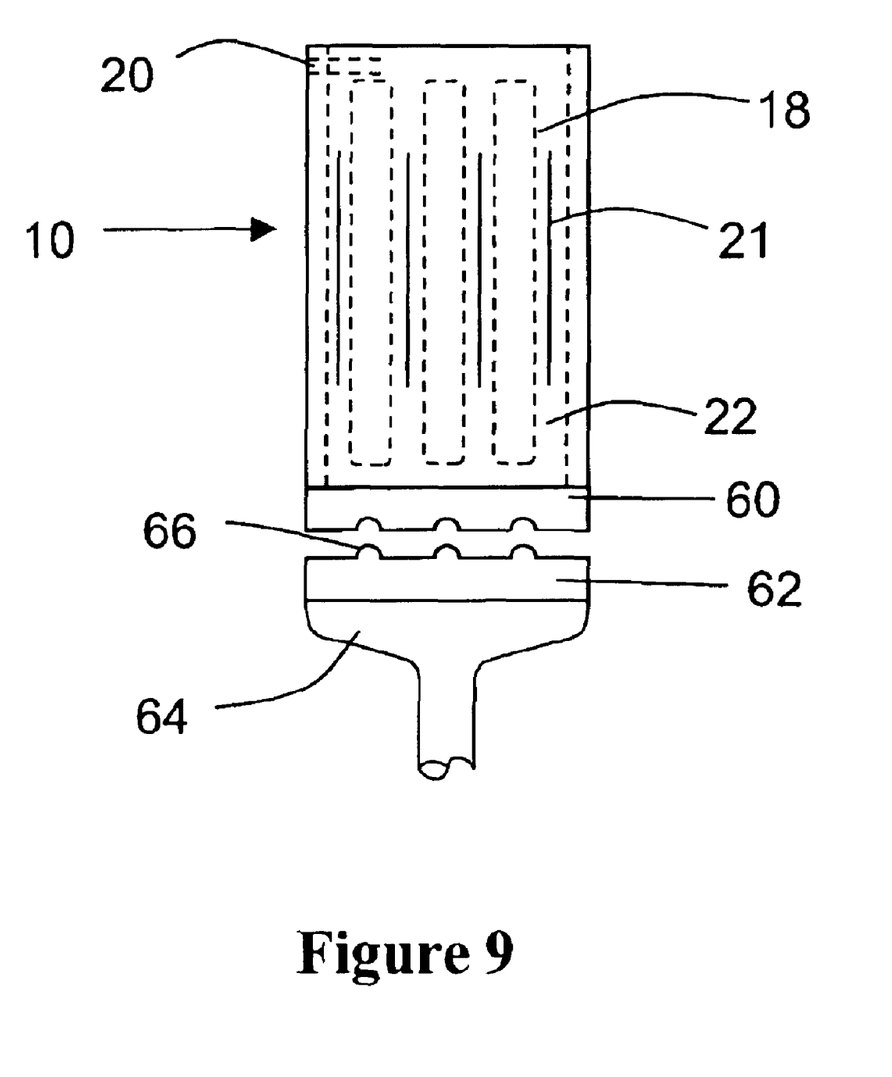
FIG. 9 is another view of the embodiment of the male urinary incontinence device of FIG. 8, showing the details of the coupling of the inflatable cuff and external catheter, as shown in uncoupled relationship to one another in the drawing.

In FIG. 9, the external catheter is shown uncoupled from the cuff, with the coupling structure shown in simplified schematic form for ease of illustration and understanding.

The specific form of coupling of the cuff and external catheter can take any of numerous suitable forms, and preferably the coupling structure for interconnecting the cuff and external catheter is of a quick-connect/quick-disconnect type, to facilitate the installation of the external catheter. Thus, the cuff can be maintained in an inflated form on the penis of a wearer for an extended time, following which the external catheter can be affixed to the cuff, and the cuff at least partially deflated to allow urinary flow through the coupled catheter to a collection bag or other means. Thereafter, the catheter can be uncoupled from the cuff, and the cuff then can be reinflated for further use.

This arrangement resolves situations where a urinary catheter cannot be worn, or situations where the collection bag attached to the exit end of the catheter has been filled by prior urine flow.

Examples of specific coupling structures that can be advantageously employed for cuff/external catheter engagement include luer-lock connectors, threaded male and female couplings, bayonet-type locking assemblies, detent structures, snap-lock fittings, ridged nozzle/hose connections, compressive ring clamps, lever-action compressive fittings, and the like. In addition, auxiliary sealing elements such as resilient O-rings and elastomeric gaskets can be provided for effecting sealing engagement between the catheter and the cuff.

The cuff can be correspondingly fitted with an adaptor, transition element, or other structural element that enables the coupling structure to be presented to structure on the catheter engageable therewith. Such adaptor can for example include the ring 60 provided on the cuff in the illustrative embodiment of FIG. 9.

Figure 10:
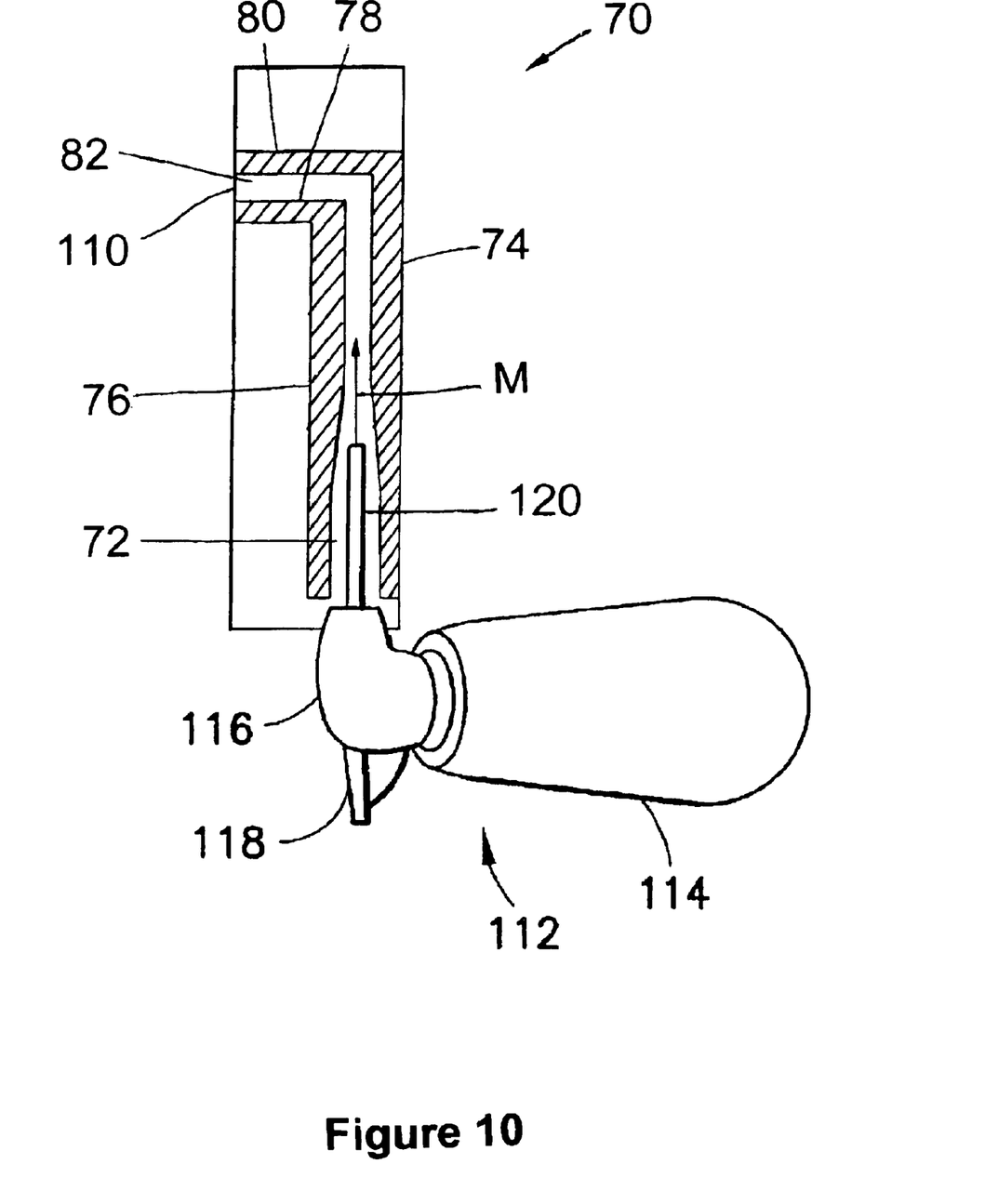
FIG. 10 is a cross-sectional view of an anti-reflux inflation valve, shown with a compressed gas inflation accessory coupled to the valve in inflating relationship therewith, such as can be advantageously used for inflation of the inflatable cuff article of the invention.

FIG. 10 is a cross-sectional view of an anti-reflux inflation valve 70, shown with a compressed gas inflation accessory 112 coupled to the valve 70 in inflating relationship therewith, such as can be employed on the cuff of the present invention for use in selectively inflating and deflating the cuff, as required. The anti-reflux valve is of a type as more fully described by the present inventors in U.S. Pat. No. 6,460,541, the disclosure of which hereby is incorporated herein by reference in its entirety for all purposes.

In inflation of the cuff, the gas feed tube 120 of the gas inflation accessory 112 is inserted into the inlet passage 72 of the anti-reflux valve 70. The gas inflation accessory 112 is equipped with a reservoir 114 of compressed inflation gas. Upon depressing the trigger 118 of the gas inflation accessory, gas from the compressed gas reservoir 114 travels through the valve head 116 and the gas feed tube 120, in the direction shown by the arrow M. The gas travels between inlet walls 74, 76 to the transition passage 82 as defined by laterally extending legs 78, 80. The gas exits the anti-reflux valve at the outlet end 110, which is positioned within the interior volume of the inflatable cuff.

As the gas pressure in the cuff increases, incident to continuing flow of inflation gas through the anti-reflux valve 70, the interior pressure of the interior volume (inflation cavity) of the cuff causes the layers of the valve structure to be biased to a closed position, as more fully described in prior U.S. Pat. No. 6,460,541, so that the anti-reflux valve is self-sealing at the desired pressure. The gas feed tube 120 then can be withdrawn from the anti-reflux valve with no substantial diminution of pressure in the inflation cavity of the cuff.

Subsequently, when it is desired to deflate the inflated cuff, it is necessary only to extend a hollow rod or stylus into the inlet passage 72 of the anti-reflux valve 70 so that the inflation air in the interior volume of the cuff can be expelled from the interior volume to the ambient environment, through the hollow lumen of the rod or stylus. For this purpose, it may be desired to detach the gas feed tube 120 from the gas inflation accessory 112 and to use it to pierce the inlet passage 72 of the anti-reflux valve 70 for effecting deflation of the cuff.

It will therefore be recognized that the cuff article of the present invention can be widely varied in form and construction, and can be fabricated for unitary packaging, installation and use, with an integrated manual inflator device as a cuff attachment. The inflatable cuff article of the invention can be provided in a kit for urinary incontinence, comprising the inflatable cuff and instructions for use thereof.

Further, while the invention has been illustratively described herein as a device for the control of urinary incontinence, it will be recognized that the cuff article can be alternatively employed for obtaining and maintaining erections, as a sexual aid, e.g., for combating erectile dysfunction, or for self-pleasuring purposes.

Accordingly, although the invention has been variously disclosed herein with reference to illustrative aspects, embodiments and features, it will be appreciated that the aspects, embodiments and features described hereinabove are not intended to limit the invention, and that other variations, modifications and other embodiments will suggest themselves to those of ordinary skill in the art. The invention therefore is to be broadly construed, consistent with the claims hereafter set forth.

What is claimed is:

1. A male incontinence control device comprising:
   an inflatable cuff adapted to encircle a shaft of a penis, said cuff having an open distal end and an open proximal end, said open distal end and open proximal end defining a length of the cuff therebetween, wherein the cuff is adapted to extend longitudinally along at least a portion of the shaft of said penis, said cuff comprising:
      an outer layer and an inner layer secured to one another to form a sealable interior volume wherein the sealable interior volume comprises a plurality of longitudinally aligned inflatable interconnected passages in spaced-apart parallel relationship to one another; and
      a selectively openable and closable valve for introducing an inflation fluid into the sealable interior volume and inflatable interconnected passages, to inflate the sealable interior volume and inflatable interconnected passages, thereby exerting a compressive pressure on the shaft of the penis.

2. The incontinence control device of claim 1, wherein the outer layer and the inner layer are each formed of polymeric film material, and said outer layer and inner layer are sealed to form the sealable interior volume and inflatable interconnected passages.

3. The incontinence control device of claim 2, wherein the outer layer and inner layer are sealed along a circumference of the cuff at locations other than the distal end and proximal end.

4. The incontinence control device of claim 3, wherein the inner layer overlaps the outer layer and the inner layer is sealed to the outer layer along a circumference of the outer layer at a distance of from about 2 mm to about 25 mm from each of the distal end and the proximal end of the cuff.

5. The incontinence control device of claim 4, wherein the inner layer is sealed along a circumference of the outer layer at a distance of from about 2 mm to about 10 mm from each of the distal end and the proximal end of the cuff.

6. The incontinence control device of claim 2, wherein the inflatable cuff defines a circumferentially continuous tubular body.

7. The incontinence control device of claim 2, wherein the inner layer has a non-slip coating thereon.

8. The incontinence control device of claim 2, wherein the polymeric film material is selected from the group consisting of: polyurethane; styrene-isoprene-styrene/styrene-butadiene-styrene compositions; plasticized polyvinylchloride; urethane/PVC blends; plasticized urethane; polyester elastomers; polyamide elastomers; olefinic polymers; and metallocene polymers.

9. The incontinence control device of claim 2, wherein each of the inner layer and outer layer is formed of a film material having a durometer value of from about 10 A to about 98 A.

10. The incontinence control device of claim 2, wherein the polymeric film material comprises polyurethane film having a durometer value not exceeding about 90 A.

11. The incontinence control device of claim 2, wherein the polymeric film material comprises material selected from the group consisting of blown film material, extruded sheet material, and solvent cast film material.

12. The incontinence control device of claim 2, wherein the polymeric film material has a thickness in a range of from about 1 to about 25 mils.

13. The incontinence control device of claim 2, wherein the polymeric film material has a thickness in a range of from about 1 to about 10 mils.

14. The incontinence control device of claim 2, wherein the polymeric film material has a thickness in a range of from about 2 to about 6 mils.

15. The incontinence control device of claim 1, wherein the outer layer, inner layer and the valve are formed of a same polymeric film material.

16. The incontinence control device of claim 1, wherein at least one of the inflatable passages contains an elongate stiffening member extending along at least a portion of the length of the cuff, wherein said at least one elongate stiffening member is formed of a material selected from the group consisting of rubber, stiff textiles, plastics, metals, and wood.

17. The incontinence control device of claim 1, wherein the inflation fluid is a gas or a liquid.

18. The incontinence control device of claim 1, wherein the inflation fluid is air.

19. The incontinence control device of claim 1, wherein the valve comprises an anti-reflux valve.

20. The incontinence control device of claim 1, having a pump coupled with the valve for inflating the sealable interior volume and inflatable interconnected passages of the inflatable cuff.

21. The incontinence control device of claim 1, wherein the distal end of the cuff features coupling structure to couple the cuff with an external catheter device.

22. The incontinence control device of claim 1, further comprising an inflatable occluder sac on an interior surface of the inner layer, arranged to communicate with the sealable interior volume and inflatable interconnected passages of the inflatable cuff, whereby when the occluder sac is inflated with the inflation fluid a preferential pressure is applied ventrally by the occluder sac to the urethra and corpus spongiosum of the penis.

23. The incontinence control device of claim 1, wherein at least one of the inflatable passages contains an elongate stiffening member extending along at least a portion of the length of the cuff.

24. The incontinence control device of claim 1, wherein each of the inflatable passages contains an elongate stiffening member extending along at least a portion of the length of the cuff.

25. A male incontinence control device comprising:
   an inflatable cuff adapted to encircle a shaft of a penis, said cuff having an open distal end and an open proximal end, said open distal end and open proximal end defining a length of the cuff therebetween, wherein the cuff is adapted to extend longitudinally along at least a portion of the shaft of said penis, said cuff comprising:
      an outer layer and an inner layer secured to one another to form a sealable interior volume wherein the sealable interior volume comprises a plurality of longitudinally aligned inflatable interconnected passages in spaced-apart parallel relationship to one another;
      a selectively openable and closable valve for introducing an inflation fluid into the sealable interior volume and inflatable interconnected passages, to inflate the sealable interior volume and inflatable interconnected passages, thereby exerting a compressive pressure on the shaft of the penis; and a pump coupled with the valve, for inflating the sealable interior volume and inflatable interconnected passages of the inflatable cuff, wherein the pump circumscribes at least a portion of the outer layer of the inflatable cuff.

26. The incontinence control device of claim 25, wherein the outer layer and the inner layer each comprise a polymeric film material, said outer layer and inner layer being sealed to form the sealable interior volume and inflatable interconnected passages of the inflatable cuff.

27. The incontinence control device of claim 26, wherein the inflatable cuff defines a circumferentially continuous tubular body.

28. The incontinence control device of claim 26, wherein the polymeric film material is selected from the group consisting of: polyurethane; styrene-isoprene-styrene/styrene-butadiene-styrene compositions; plasticized polyvinylchloride; urethane/PVC blends; plasticized urethane; polyester elastomers; polyamide elastomers; olefinic polymers; and metallocene polymers.

29. The incontinence control device of claim 25, wherein at least one of the inflatable passages contains an elongate stiffening member extending along at least a portion of the length of the cuff.

30. The incontinence control device of claim 25, wherein the inflation fluid is air.

31. The incontinence control device of claim 25, wherein the valve comprises an anti-reflux valve.

32. The incontinence control device of claim 25, wherein the distal end of the cuff is provided with coupling structure to couple the cuff with an external catheter device.

33. A male incontinence control device comprising:

an inflatable cuff adapted to encircle a shaft of a penis, said cuff having an open distal end and an open proximal end, said open distal end and open proximal end defining a length of the cuff therebetween, wherein the cuff is adapted to extend longitudinally along at least a portion of the shaft of said penis, said cuff comprising:

an outer layer and an inner layer secured to one another to form a sealable interior volume wherein the sealable interior volume comprises a plurality of longitudinally aligned inflatable interconnected passages in spaced-apart parallel relationship to one another;

a selectively openable and closable valve for introducing an inflation fluid into the sealable interior volume and inflatable interconnected passages, to inflate the sealable interior volume and inflatable interconnected passages, thereby exerting a compressive pressure on the shaft of the penis; and an external catheter matably engageable with the distal end of the cuff.

34. The incontinence control device of claim 33, wherein each of the outer layer and the inner layer comprises polymeric film material, and said outer layer and inner layer are sealed to form the sealable interior volume and inflatable interconnected passages.

35. The incontinence control device of claim 34, wherein the inflatable cuff defines a circumferentially continuous tubular body.

36. The incontinence control device of claim 34, wherein the polymeric film material is selected from the group consisting of: polyurethane; styrene-isoprene-styrene/styrene-butadiene-styrene compositions; plasticized polyvinylchloride; urethane/PVC blends; plasticized urethane; polyester elastomers; polyamide elastomers; olefinic polymers; and metallocene polymers.

37. The incontinence control device of claim 33, wherein at least one of the inflatable passages contains an elongate stiffening member extending along at least a portion of the length of the cuff.

38. The incontinence control device of claim 33, wherein the sealable interior volume is inflated with air.

39. The incontinence control device of claim 33, wherein the valve comprises an anti-reflux valve.

40. The incontinence control device of claim 33, further comprising a pump for inflating the sealable interior volume of the inflatable cuff.

41. The incontinence control device of claim 33, further comprising a first rigid collar at the distal end of the inflatable cuff and a second rigid collar on the external catheter, wherein the first and second collars include matably engageable coupling structure adapted for interconnection of the first and second collars.

42. A method for using a urinary incontinence device comprising a circumferentially continuous inflatable cuff, a selectively openable and closeable valve on the inflatable cuff for inflating and deflating said cuff, and a plurality of interconnected inflatable passages interiorly disposed in the inflatable cuff for stiffening the cuff when inflated and applying selective pressure to a penis of a male wearer to control urinary incontinence of said wearer, wherein the method comprises the steps of:

installing the inflatable cuff on the shaft of the penis anterior to the glans of the penis, with the inflatable cuff circumscribing the penis, wherein the inflatable cuff comprises a distal end, a proximal end, an outer layer and an inner layer, wherein the outer layer and inner layer are sealed along a circumference of the inflatable cuff at locations other than the distal end and the proximal end; and inflating the inflatable cuff with an inflation fluid to compressively occlude the urethral passage of the penis.

43. The method of claim 42, wherein at least one of the inflatable passages contains an elongate stiffening member extending along at least a portion of the length of the cuff.

44. A kit for urinary incontinence comprising an inflatable cuff according to claim 25 and instructions for use thereof.

* * * * *